United States Patent [19]
Gracilla

[11] Patent Number: 5,669,908
[45] Date of Patent: Sep. 23, 1997

[54] CAST BRACE FOR FEMORAL SHAFT FRACTURES IN CHILDREN

[76] Inventor: R. V. Gracilla, 302 Clay Furnace Rd., Sharpsville, Pa. 16150

[21] Appl. No.: 585,512

[22] Filed: Jan. 16, 1996

[51] Int. Cl.$^6$ .................................................. A61F 5/04
[52] U.S. Cl. .......................... 606/53; 606/56; 606/57; 602/23
[58] Field of Search ............................. 606/56, 57, 58, 606/59, 60, 54, 53; 602/9, 10, 11, 12, 23, 3, 5, 8

[56] References Cited

U.S. PATENT DOCUMENTS

| | | | |
|---|---|---|---|
| 491,271 | 2/1893 | Rowley | 602/23 |
| 1,399,606 | 12/1921 | Ferragamo | 602/23 |
| 1,577,782 | 3/1926 | Atkinson | 602/23 |
| 1,663,921 | 3/1928 | Pierce . | |
| 2,024,325 | 12/1935 | Allen | 606/56 |
| 2,048,832 | 7/1936 | Wiltrout | 602/8 |
| 2,055,024 | 9/1936 | Bittner, Jr. | 606/56 |
| 2,110,414 | 3/1938 | Bell | 602/8 |
| 2,204,266 | 6/1940 | Wilcox | 606/56 |
| 2,301,534 | 11/1942 | Goodwin . | |
| 2,406,987 | 9/1946 | Anderson | 606/59 |
| 3,727,610 | 4/1973 | Riniker | 606/56 |
| 3,977,397 | 8/1976 | Kalnberz et al. | 606/57 |
| 4,350,153 | 9/1982 | Borschneck . | |
| 5,162,039 | 11/1992 | Dahners . | |

*Primary Examiner*—Michael Buiz
*Assistant Examiner*—Julian W. Woo
*Attorney, Agent, or Firm*—Harpman & Harpman

[57] ABSTRACT

A cast brace for use for the treatment of children having femoral shaft fractures. The brace includes a main support bracket adapted to extend from a support cast. A tension assembly extending from the brace to a support yolk applying tension to a K-wire extending transversely through the leg specifically the tibia adjacent the tip of the medial malleolus secured to a traction bow. Adjustability of the traction tension to facilitate proper bone alignment and to expedite the time required to maintain the limb in traction.

9 Claims, 4 Drawing Sheets

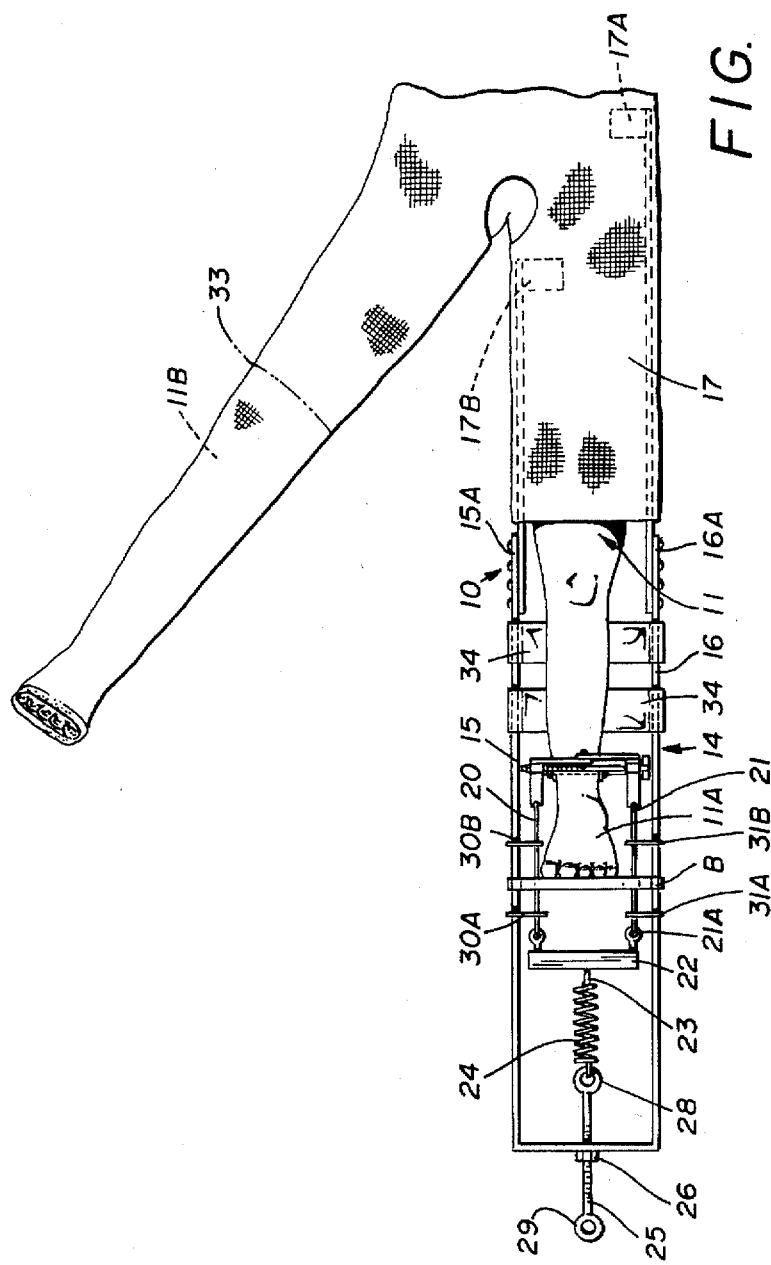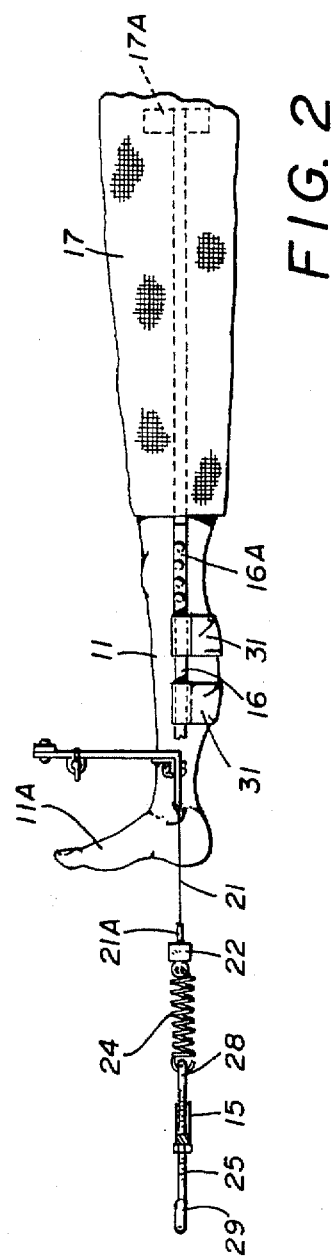

CAST BRACE FOR FEMORAL SHAFT FRACTURES IN CHILDREN

BACKGROUND OF THE INVENTION

2. Technical Field

This device relates to leg splints or traction devices to hold into position the effected area during the healing process especially in children.

2. Description of Prior Art

Prior art devices of this type have been directed to immobilization systems that hold and support the injured limb of the patient in an aligned position under a select amount of traction pressure, see for example U.S. Pat. Nos. 1,663,921, 2,301,534, 4,350,153 and 5,162,039.

In U.S. Pat. No. 1,663,921 a limb brace can be seen having struts embedded in a leg cast with an adjustable tension alignment bracket engaged on a foot harness pulling on the leg.

U.S. Pat. No. 2,301,534 discloses a traction splint having a leg engagement frame, a portion of which is positioned under the effective leg to supply stabilization pressure on the frame. A shoe engagement bracket inputs adjustable pressure on the leg through an adjustment arm in the lower end of the engagement frame.

U.S. Pat. No. 4,350,153 claims a leg splint having a leg engagement frame with a spring bracket to provide constant pressure to the foot by pulling with an engagement strap.

In U.S. Pat. No. 5,162,039 a distraction and reduction device is illustrated wherein a single support arm is wedgeably engaged in the patient's groin with a Kirschner-type wire bow adjustably connected to the support arm by an offset secondary support arm.

SUMMARY OF THE INVENTION

An adjustable cast brace for femoral shaft fractures in children to expedite treatment and shorten hospital stays. The cast brace consist of a main brace assembly extending from a support cast above the fracture. A wire bow is attached through the tibia just anterior to the anterior border of the fibia. Engagement wires extend from the support bow to a resilient tension adjustment secured to the cast brace portion in spaced longitudinal relation to the foot portion of the patient.

DESCRIPTION OF THE DRAWINGS

FIG. 1 is a perspective view illustrating the use of the cast brace to distract a bone fracture;

FIG. 2 is a side elevational view of the cast brace in use with portions broken away for clarity;

DESCRIPTION OF THE PREFERRED EMBODIMENT

Figure 3:
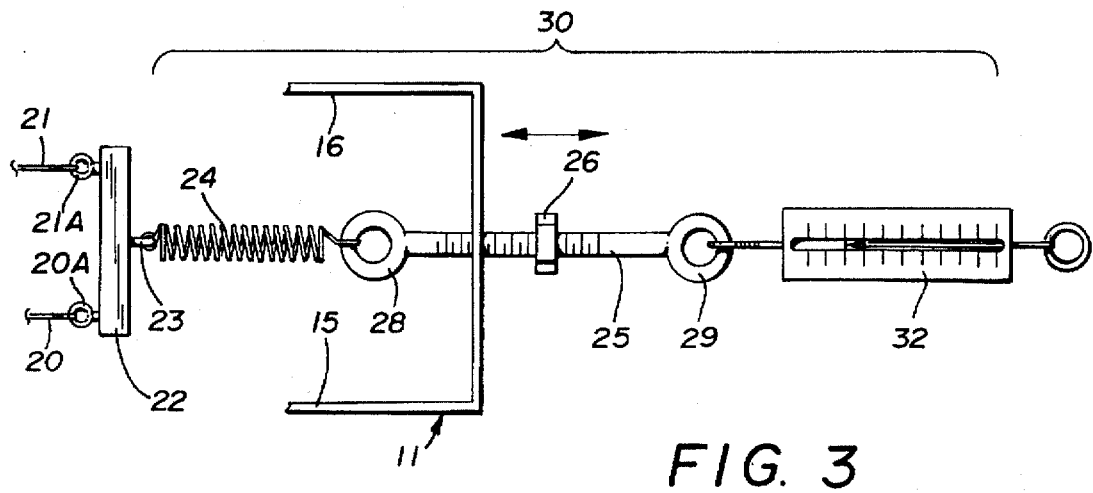
FIG. 3 is an enlarged partial top plan view of a tension adjustment assembly of the device of the invention.

Referring to FIGS. 1, 2, 4, and 5 of the drawings, a cast brace 10 can be seen for stabilization and distraction of a lower leg portion of a human leg 11 and foot 11A with a tibia 12 and a fibia 13 bones therein to aid in the treatment of a bone fracture thereto.

The cast brace 10 includes a main support bracket 14 with adjustable bracket portions 15 and 16 extending along the same transverse plane of the leg 11. The free ends of the bracket portions 15 & 16 are longitudinally adjustable at 15A and 16A respectively and terminate within a hip and leg cast 17 at 17A and B maintaining the opposing leg L in abduction of about 45 degrees to the treatment leg 11. The cast 17 on the treatment leg 11 extends to a point just above the knee K.

The distal portion of the support bracket 14 integrally connects the bracket portions 15 and 16 considerably beyond the foot 11A of the leg 11. The bracket portions 15 and 16 extend in longitudinal alignment with the leg 11 as will be well known to those skilled in the art.

Figure 4:
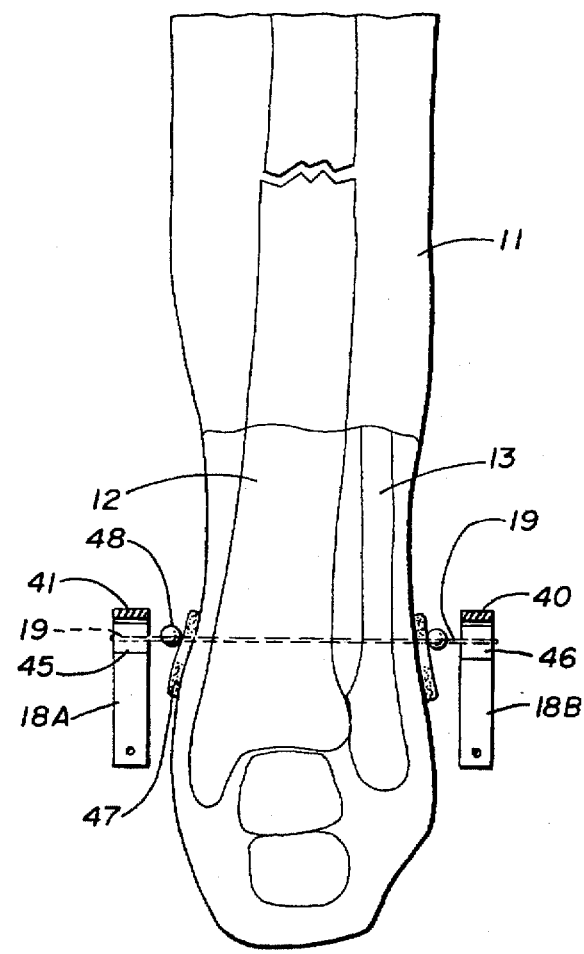
FIG. 4 is an enlarged diagrammatical illustration of a human leg joint illustrating point of attachment of the invention on line 4—4 of FIG. 6.
Figure 5:
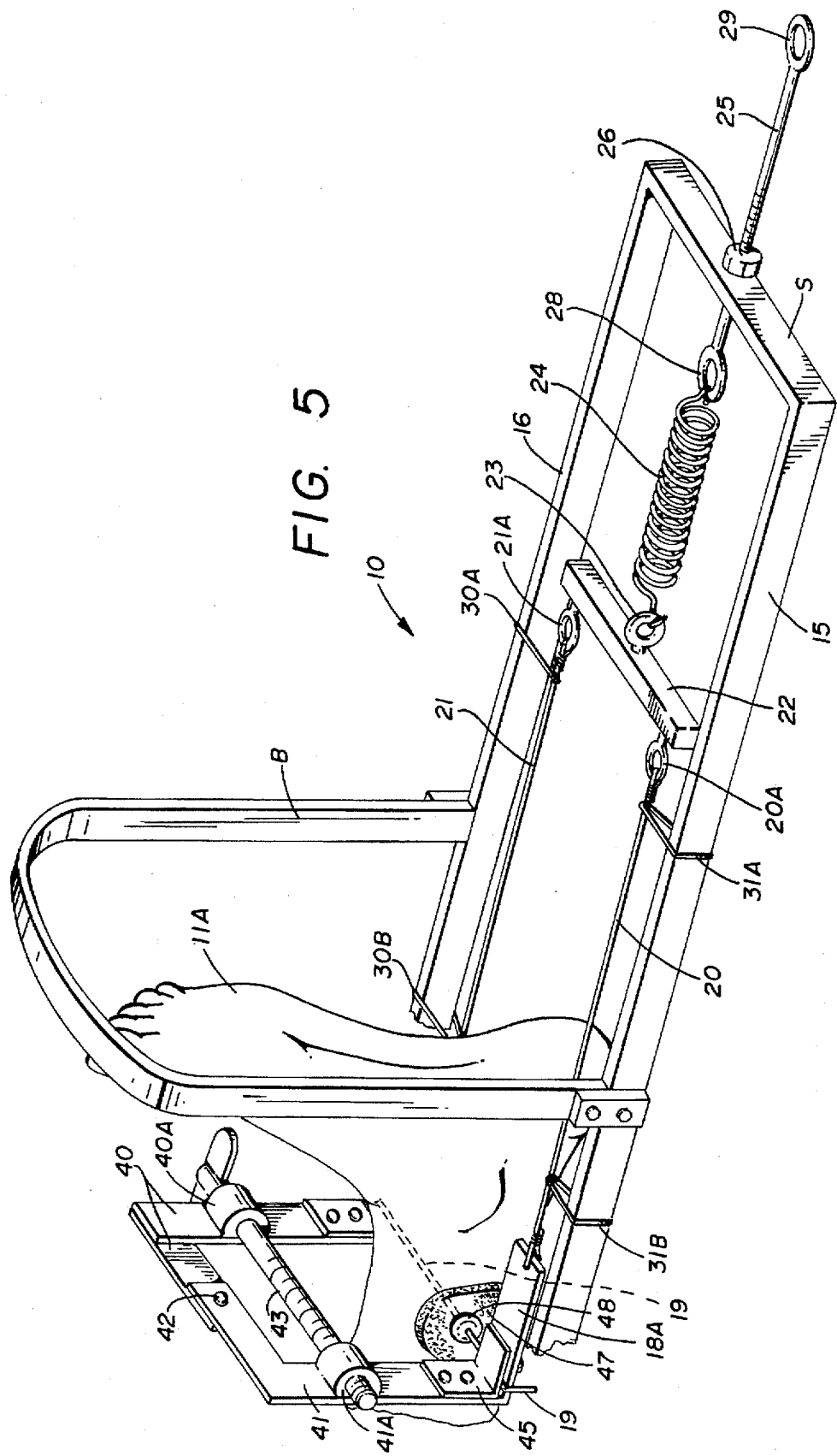
FIG. 5 is an enlarged perspective view of the tension adjustment assembly of the invention.
Figure 8:
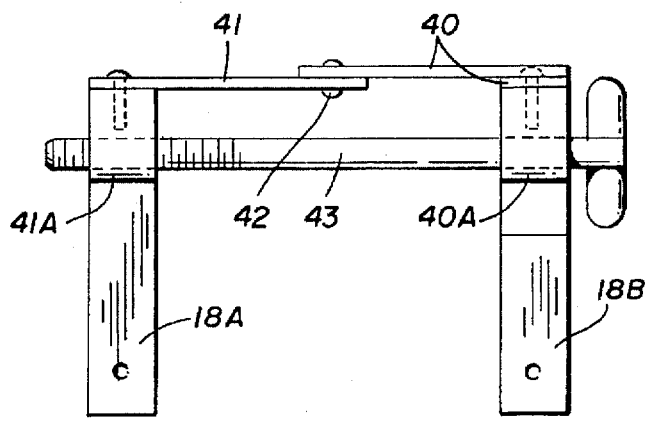
FIG. 8 is an enlarged side plan view of the wire bow portion illustrated in FIG. 6 independent of the patient engaged thereon.
Figure 6:
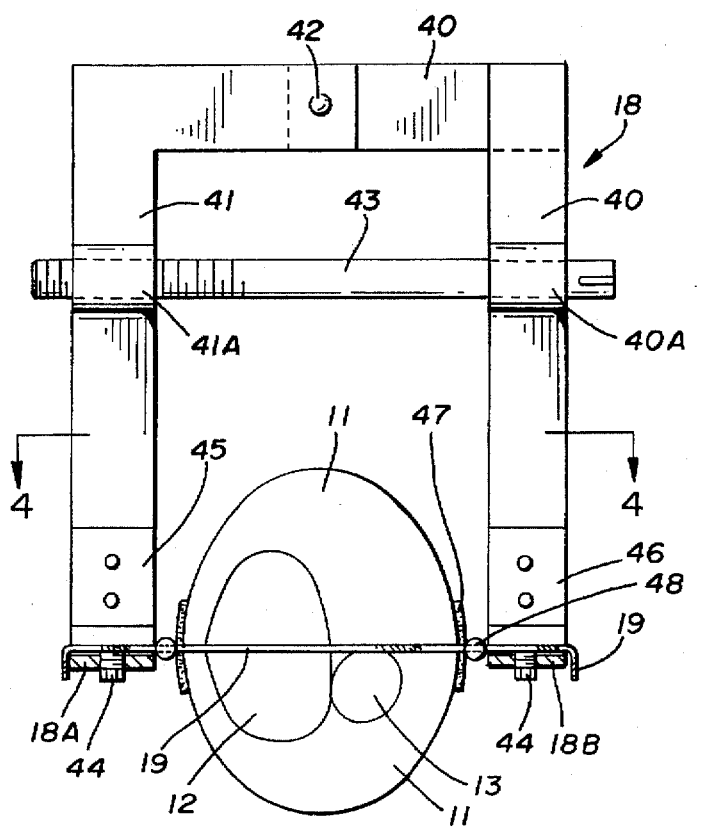
FIG. 6 is an enlarged elevational view of a wire bow portion engaged on a patient.
Figure 7:
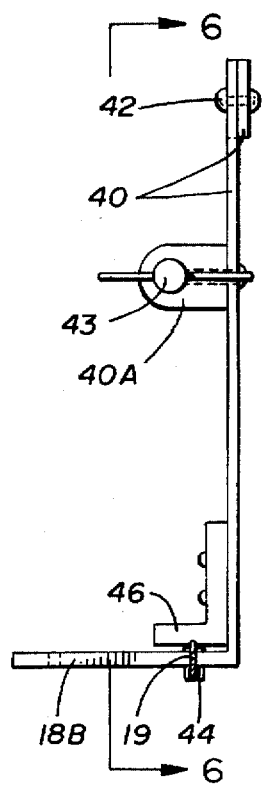
FIG. 7 is an enlarged top plan view of the wire bow portion stated in FIG. 6 independent of the patient.

A "Kirschner" type wire bow 18 assembly, best seen in FIGS. 6, 7, and 8 of the drawings, is positioned on the leg 11 with a "Kirschner" wire 19, shown in broken lines, best seen in FIGS. 4 and 5 of the drawings, extending through the leg 11 approximately five to eight centimeters proximal to the tip of the medial malleolus through the tibia 12 along the mid-axial line of the leg 11, perpendicular to the longitudinal axis of a point just anterior to the anterior border of the fibia 13 and through the skin laterally thereof.

Referring now to FIGS. 5, 6, 7, and 8 of the drawings, the K-wire bow assembly 18 can be seen having a pair of support elements 40 and 41 pivoted together by a pivot pin 42 defining a generally inverted U-shaped configuration with respective right angular extending engagement arms 18A and 18B extending outwardly therefrom co-planar with the leg's longitudinal axis.

Each of the support elements 40 and 41 have an adjustment receiving lug 40A and 41A thereon through which is threadably positioned an adjustment rod 43.

The k-wire 19 is secured between said engagement arms 18A and 18B by set screws 44 threadably engaged therethrough and wire engaging brackets 45 and 46 secured to the respective support elements 40 and 41 as will be well understood by those skilled in the art, best seen in FIGS. 6 and 7 of the drawings. It will be evident from the above description that the relative tension on the K-wire can be readily adjusted by the adjustment rod 43 hereinbefore described.

In practice, cloth pads 47 about the K-wire 19 are held against the patient's foot 11A at the respective points of wire entry and exit wounds through the leg by adjustment spacer beads 48 on the K-wire 19 outboard of the respective pads 47. The entry and exit points are treated in an A-typical manner and are covered with Vaseline gauze, dry gauze dressing as will be well understood by those skilled in the art utilizing the pads 46 to hold the dressings in place against the exit and entry points.

A pair of engagement wires 20 and 21 extend from the free ends of the respective arms 18A and B in spaced parallel relation to one another and are secured to a yoke element 22 extending transversely in spaced planar relation to respective bracket elements 15 and 16.

The engagement wires 20 and 21 are secured in oppositely disposed spaced relation to one another on said yoke at attachment fittings 20A and 21A.

An attachment element 23 is positioned midway along said yoke in central relation thereto to which is secured a resilient spring 24 opposite said engagement wires 20 and 21.

Referring now to FIGS. 3 and 5 of the drawings, the cast brace 10 of the invention can be seen with the distal portion of the support bracket having a shaft 25 extending through a bore centrally positioned therein.

The shaft 25 is threadably engaged by a position nut 26 which is engageable on the outer surface (S) of the distal portion of the support bracket 10. The shaft 25 is characterized by eyelets 28 and 29 on its respective ends.

The spring 24 is engageable on the eyelet 28 of the shaft 25 defining a tension adjustment on the Kirschner wire bow 18 via the interconnected yoke 22 as hereinbefore described.

Pairs of guide wires 30 A and B and 31 A and B extend inwardly in spaced parallel relation from around the respective bracket 15 and 16 and about the engagement wires 20 and 21 for lateral and transverse positioning between the respective brackets. The engagement wires 20 and 21 are of a sufficient cross-section dimension to impart relative stiffness thereto assuring an interconnecting adjustable relationship between the Kirschner bow 18 and the hereinbefore described yoke 22, spring 24 and screw shaft 25 relationship defining a spring tension adjustment assembly 30 as illustrated in FIG. 3 of the drawings.

Referring back to FIGS. 1 and 2 of the drawings, it will be seen in use that a plurality of fabric support bands 34 extend transversely between said respective support bracket portions 15 and 16 so as to cradle and support the leg 11 in the desired position within the cast brace 10. A foot board bracket B extends from the respective support bracket portions 15 and 16 between the guide wire pairs 31A and 31B to support a drop foot board B (not shown) or equivalent as will be well understood by those skilled in the art.

It will be apparent from the above description that the relative tension applied by the device of the invention can be measured by utilizing a spring scale 32 as illustrated in FIG. 3 of the drawings and that appropriate adjustments to the tension imparted can be made by adjusting the shaft 25, by rotation and repositioning of the nut 26 thereon.

By maintaining a constant traction pressure on the leg 11 expedited healing can take place to the fracture assuring a shortened hospital stay for the patient.

After a prescribed time period, the device of the invention is removed and the cast 17 is extended on the patient's leg 11 to the foot 11A while the opposing leg L cast is cut short as indicated by broken line 33 in FIG. 1 of the drawings.

To determine the proper tension to be applied by the cast brace 10 of the invention the relative bone position is confirmed periodically by x-ray achieving the desired fracture element position and maintenance while the cast brace 10 is in use.

It will thus be seen that a new and novel fracture cast brace for femoral shaft fracture in children has been illustrated and described and it will be apparent to those skilled in the art that various changes and modifications may be made therein without departing from the spirit of the invention, therefore I claim:

I claim:

1. A surgical device for setting fractures of a human leg comprises in combination, a pair of parallel longitudinally adjustable support brackets extending along a patient's leg, said support brackets interconnected at their distal end portion a cast on said patient engaging said support brackets, a bow with a wire engageable through a portion of said patient's leg, a tension adjustment means for applying distal direct force to said leg on said distal end portion of said support brackets in spaced longitudinal relation to said leg, rigid support wires extending from said bow in parallel spaced co-planar alignment with one another and the longitudinal axis of said leg, and an intermediate yoke engageable by said rigid support wires and said tension adjustment means on said support brackets.

2. The surgical device set forth in claim 1 further comprises guide means on said respective support brackets engageable about said respective rigid support wires in spaced relation from said leg engagement means and said intermediate yoke.

3. The surgical device set forth in claim 1 wherein said cast extends midway down said leg.

4. The surgical device set forth in claim 1 wherein said wire is engageable through a tibia five to eight centimeters proximal to the tip of the medial malleolus anterior to the anterior border of a fibia.

5. The surgical device set forth in claim 1 wherein said tension adjustment means comprises a shaft extending through the distal end of said support brackets resilient means attached to one end of said shaft, a retaining fitting threadably on said shaft engageable on said distal portion of said support brackets opposite said resilient means.

6. The surgical device set forth in claim 1 further comprises leg support bands on said support bracket for engagement with said leg.

7. The surgical device set forth in claim 4 wherein said bow comprises pivoted support elements, adjustable interconnected means on said support elements, wire engagement arms extending from said support elements, and means for securing said wire between said engagement arms.

8. The surgical device set forth in claim 5 wherein said resilient means attached to one end of said shaft comprises a spring extending from said yoke.

9. The surgical device set forth in claim 7 wherein said means for securing said wire between said engagement arms comprises wire engaging brackets extending between said support elements and respective wire engagement arms.

* * * * *